US010888380B2

(12) United States Patent
Bor et al.

(10) Patent No.: US 10,888,380 B2
(45) Date of Patent: Jan. 12, 2021

(54) SYSTEMS AND METHODS FOR INTRAOCULAR LENS SELECTION

(71) Applicant: Alcon Research, Ltd., Fort Worth, TX (US)

(72) Inventors: Zsolt Bor, San Clemente, CA (US); Imre Hegedus, Aliso Viejo, CA (US)

(73) Assignee: Alcon Inc.

(*) Notice: Subject to any disclaimer, the term of this patent is extended or adjusted under 35 U.S.C. 154(b) by 110 days.

(21) Appl. No.: 16/171,515

(22) Filed: Oct. 26, 2018

(65) Prior Publication Data

US 2020/0015894 A1   Jan. 16, 2020

Related U.S. Application Data

(60) Provisional application No. 62/697,367, filed on Jul. 12, 2018.

(51) Int. Cl.
 *A61B 34/10* (2016.01)
 *G06T 7/73* (2017.01)
 *G06T 7/00* (2017.01)

(52) U.S. Cl.
 CPC ............ *A61B 34/10* (2016.02); *G06T 7/0012* (2013.01); *G06T 7/73* (2017.01); *A61B 2034/104* (2016.02);
 (Continued)

(58) Field of Classification Search
 None
 See application file for complete search history.

(56) References Cited

U.S. PATENT DOCUMENTS 5,282,852 A * 2/1994 Capetan ............... A61B 3/10
                                                      623/6.11
5,958,520 A * 9/1999 Cook ................... C23C 4/12
                                                      29/888.061
(Continued)

FOREIGN PATENT DOCUMENTS

DE    102015225759 A1    6/2017
EP       2605696 A1      6/2013
(Continued)

OTHER PUBLICATIONS

Estimation of intraocular lens position from full crystalline lens geometry: towards a new generation of intraocular lens ; Martinez Enriquez ; Mar. 6, 2018 (Year: 2018).*

(Continued)

*Primary Examiner* — Nancy Bitar
(74) *Attorney, Agent, or Firm* — Joseph Weatherbee, Esq.

(57) ABSTRACT

Systems and methods for intraocular lens selection include receiving, by one or more computing devices implementing a prediction engine, pre-operative multi-dimensional images of an eye; extracting, by the prediction engine, pre-operative measurements of the eye based on the pre-operative images; estimating, by the prediction engine using a prediction model based on a machine learning strategy, a post-operative position of an intraocular lens based on the extracted pre-operative measurements; selecting a power of the intraocular lens based on the estimated post-operative position of the intraocular lens; and selecting the intraocular lens based on the selected power. In some embodiments, the systems and methods further include receiving post-operative multi-dimensional images of the eye after implantation of the selected intraocular lens, extracting post-operative measurements of the eye, and updating the prediction model based (Continued)

on the pre-operative measurements and the post-operative measurements.

17 Claims, 6 Drawing Sheets

(52) U.S. Cl.
CPC ... *A61B 2034/105* (2016.02); *A61B 2034/107* (2016.02); *A61B 2034/108* (2016.02); *G06T 2207/20081* (2013.01); *G06T 2207/30041* (2013.01)

(56) References Cited

U.S. PATENT DOCUMENTS

| | | | | |
|---|---|---|---|---|
| 7,241,009 | B2* | 7/2007 | Kornfield | G02B 1/043 351/159.73 |
| 9,271,829 | B2 | 3/2016 | Bühren et al. | |
| 2014/0192317 | A1* | 7/2014 | Buhren | A61F 2/16 351/205 |
| 2017/0316571 | A1 | 11/2017 | Martínez-enríquez et al. | |
| 2018/0092524 | A1* | 4/2018 | Ng | G09B 23/30 |
| 2019/0209242 | A1* | 7/2019 | Padrick | A61B 34/10 |

FOREIGN PATENT DOCUMENTS

| | | |
|---|---|---|
| GB | 2488802 A | 9/2012 |
| WO | 2010109020 A1 | 9/2010 |

OTHER PUBLICATIONS

Intraocular lens calculation accuracy limits in normal eyes; Paul-Rolf Preußner, MD, PhD, Thomas Olsen, MD, Peter Hoffmann, MD, Oliver Findl, MD; 2008 (Year: 2008).*
Cooke, et al., "Comparison of 9 Intraocular Lens Power Calculation Formulas," J. Cataract Refract. Surg. vol. 42, pp. 1157-1164, 2016.
Goto, et al., "Prediction of Postoperative Intraocular Lens Position with Angle-to-Angle Depth Using Anterior Segment Optical Coherence Tomography," Ophthalmology vol. 123, pp. 2474-2480, 2016.
Kane, et al., "Intraocular Lens Power Formula Accuracy: Comparison of 7 Formulas," J. Cataract Refract. Surg. vol. 42, pp. 1490-1500, 2016.
Martinez-Enriquez, et al. "Estimation of Intraocular Lens Position from Full Crystalline Lens Geometry: Towards a New Generation of Intraocular Lens Power Calculation Formulas," Nature Scientific Reports vol. 8:9829, 2018.
Melles, et al. "Accuracy of Intraocular Lens Calculation Formulas," Ophthalmology vol. 125(2), pp. 1-10.
Norrby, et al. "Prediction of the True IOL Position," Ophthalmology vol. 101, pp. 1440-1446, 2017.
Olsen, "Calculation of Intraocular Lens Power: A Review," Acta Ophthalmol Scand, vol. 85, pp. 472-485, 2007.
Martinez-Enriquez Eduardo et al: "Estimation of intraocular lens position from full crystalline lens geometry: towards a new generation of intraocular lens power calculation formulas",XP002796277, Database Biosis [online] Biosciences Information Service, Philadelphia, PA, US; Scientific Reports, vol. 8, (Jun. 29, 2018), Article No. 9829, ISSN: 2045-2322.

* cited by examiner

SYSTEMS AND METHODS FOR INTRAOCULAR LENS SELECTION

CROSS-REFERENCE TO RELATED APPLICATIONS

This application claims the benefit of U.S. Provisional Patent Application No. 62/697,367 filed Jul. 12, 2018 and entitled "OPTHALMIC IMAGING SYSTEM FOR INTRAOCULAR LENS POWER PREDICTION" which is hereby incorporated by reference in its entirety.

BACKGROUND

Field of the Disclosure

The present disclosure relates to systems and methods of using multi-dimensional images of an eye to aid in the selection of an intraocular lens to be implanted.

Description of Related Art

Cataract surgery involves removing the natural lens of an eye and, in most cases, replacing the natural lens with an artificial intraocular lens (IOL). To achieve an optimal post-operative visual outcome, a good pre-operative surgical plan is crucial. Some of the important pre-operative planning decisions are the selection of an appropriate IOL power and an estimate of an effective lens position (ELP) which are determined according to measurements taken of the patient's eye's anatomical and optical characteristics and used in one or more IOL power calculation formulas. See, for example, Cooke, et al., "Comparison of 9 Intraocular Lens Power Calculation Formulas," J. Cataract Refract. Surg. Vol. 42, pp. 1157-64, 2016; Goto, et al., "Prediction of Postoperative Intraocular Lens Position with Angle-to-Angle Depth Using Anterior Segment Optical Coherence Tomography," Ophthalmology Vol. 123, pp. 2474-80, 2016; Kane, et al., "Intraocular Lens Power Formula Accuracy: Comparison of 7 Formulas," J. Cataract Refract. Surg. Vol. 42, pp. 1490-1500, 2016; Martinez-Enriquez, et al. "Estimation of Intraocular Lens Position from Full Crystalline Lens Geometry: Towards a New Generation of Intraocular Lens Power Calculation Formulas," Nature Scientific Reports Vol. 8:9829, 2018; Melles, et al. "Accuracy of Intraocular Lens Calculation Formulas," Ophthalmology Vol. 125(2), pp. 1-10; Norrby, et al. "Prediction of the True IOL Position," Ophthalmology Vol. 101, pp. 1440-46, 2017; and Olsen, "Calculation of Intraocular Lens Power: A Review," Acta Ophthalmol Scand, Vol. 85, pp. 472-85, 2007, each of which is hereby incorporated by reference in its entirety.

Typically, the measurements used in the IOL prediction formulas are one-dimensional measurements taken on the optical axis using an optical and/or ultrasound biometer. These traditional measurement practices lead to inaccuracy in the ELP which, in turn, leads to the selection of an IOL power that results in a suboptimal vision outcome for the patient.

Therefore, there is a need in the art for techniques for preoperatively assessing a patient's eye to measure anatomical parameters that may be used to better select an intraocular lens for implantation that leads to optimized vision outcomes for patients.

SUMMARY

According to some embodiments, a method includes receiving, by one or more computing devices implementing a prediction engine, one or more pre-operative multi-dimensional images of an eye; extracting, by the prediction engine, one or more pre-operative measurements of the eye based on the one or more pre-operative images of the eye; estimating, by the prediction engine using a first prediction model based on a machine learning strategy, a post-operative position of an intraocular lens based on the one or more extracted pre-operative measurements of the eye; selecting a power of the intraocular lens based on at least the estimated post-operative position of the intraocular lens; and selecting the intraocular lens based on at least the selected power.

According to some embodiments, a prediction engine includes one or more processors. The prediction engine is configured to receive one or more pre-operative multi-dimensional images of an eye obtained by a diagnostic device; extract one or more pre-operative measurements of the eye based on the one or more pre-operative images of the eye; estimate, using a first prediction model based on a machine learning strategy, a post-operative position of an intraocular lens based on the one or more extracted pre-operative measurements of the eye; recommend a power of the intraocular lens based on at least the estimated post-operative position of the intraocular lens; and provide the recommended power to a user to facilitate selection of the intraocular lens for implantation.

According to some embodiments, a non-transitory machine-readable medium comprising a plurality of machine-readable instructions which when executed by one or more processors are adapted to cause the one or more processors to perform a method. The method includes receiving one or more pre-operative multi-dimensional images of an eye; extracting one or more pre-operative measurements of the eye based on the one or more pre-operative images of the eye; estimating, using a prediction model based on a machine learning strategy, a post-operative position of an intraocular lens based on the one or more extracted pre-operative measurements of the eye; recommending a power of the intraocular lens based on at least the estimated post-operative position of the intraocular lens; and providing the recommended power to a user to facilitate selection of the intraocular lens for implantation.

BRIEF DESCRIPTION OF THE DRAWINGS

For a more complete understanding of the present technology, its features, and its advantages, reference is made to the following description, taken in conjunction with the accompanying drawings.

Figure 1:
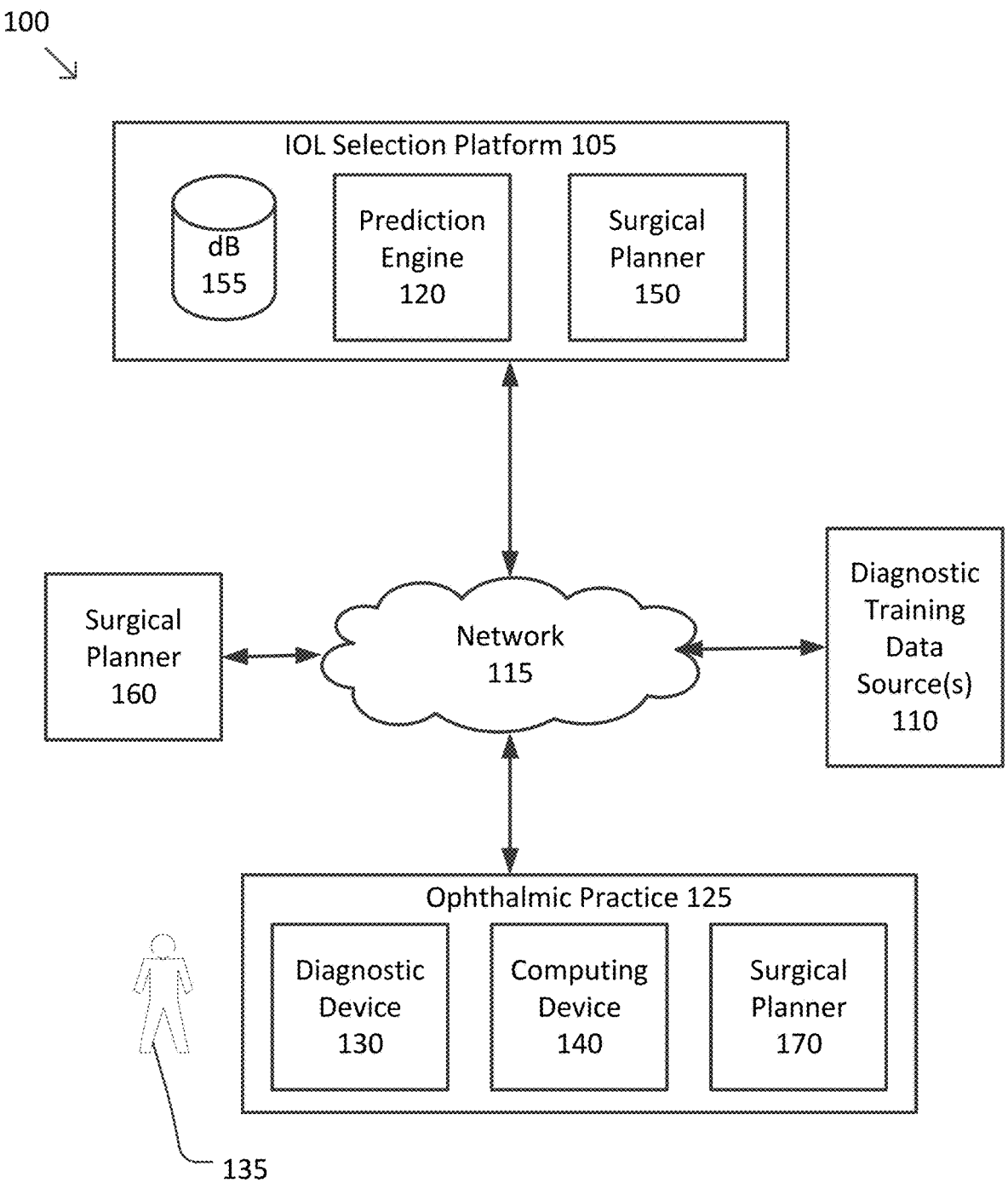
FIG. 1 is a diagram of a system for IOL selection according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The technology described below involves systems and methods of using a collection of pre- and post-operative multi-dimensional images of the eyes of training patients with supervised machine learning to predict a post-operative anterior chamber depth, a power for an intraocular lens (IOL) of a new patient, and a post-operative manifest refraction spherical equivalent (MRSE).

As explained above, IOL power predictions have traditionally relied on measurements from an optical and/or ultrasound biometer. Some of the more commonly used measured characteristics of the eye used in IOL power calculation formulas are the corneal radius of curvature (K), the axial length (AL) (which includes an eye's anterior chamber depth (ACD)), lens thickness, vitreous chamber depth, the horizontal distance between the borders of the corneal limbus (also known as the corneal white-to-white distance), and/or the like.

However, two- or three-dimensional measurements of a patient's eye provide additional anatomical detail that may be used to better predict a post-operative anterior chamber depth (also referred to as an estimated lens position (ELP)) and IOL power. In some examples, use of a better predictive mechanism may be used to improve post-operative refractive outcome in the MRSE.

Some embodiments of the present disclosure involve obtaining pre- and post-operative diagnostic training data in the form of two- or three-dimensional images of the eyes of a collection of patients, obtaining a plurality of measurements from pre-operative diagnostic images of a new patient, and using one or more machine learning techniques to create a prediction model for calculating an estimate of post-operative anterior chamber depth ($ACD_{post}$) for the new patient based on a plurality of measurements of the new patient. The postoperative anterior chamber depth may then be used to select an appropriate power for the implanted IOL.

FIG. 1 illustrates a system 100 for a system for IOL selection according to some embodiments. System 100 includes an IOL selection platform 105 coupled with one or more diagnostic training data sources 110 via a network 115. In some examples, network 115 may include one or more switching devices, routers, local area networks (e.g., an Ethernet), wide area networks (e.g., the Internet), and/or the like. Each of the diagnostic training data sources 110 may be a database, a data repository, and/or the like made available by an, ophthalmic surgery practice, an eye clinic, a medical university, an electronic medical records (EMR) repository, and/or the like. Each of the diagnostic training data sources 110 may provide IOL selection platform 105 with training data in the form of one or more of multi-dimensional images of patients' pre- and post-operative eyes, surgical planning data, surgical console parameter logs, surgical complication logs, patient medical history, patient demographic data, and/or the like. IOL selection platform 105 may store the training data in one or more databases 155 which may be configured to anonymize, encrypt, and/or otherwise safeguard the training data.

IOL selection platform 105 includes a prediction engine 120 which may (as explained in greater detail below) process the received training data, extract measurements from the multi-dimensional images, perform raw data analysis on the training data, train machine learning algorithms and/or models to predict $ACD_{post}$ based on pre-operative measurements, and iteratively refine the machine learning to optimize $ACD_{post}$ prediction for use with future patients to improve their post-implantation outcomes (e.g., better optical properties of the eye with the implanted IOL). In some examples, prediction engine 120 may use one or more prediction models (e.g., one or more a neural networks) that are trained based on pre-operative measurements and corresponding post-operative outcomes obtained from the one or more diagnostic training data sources 110.

IOL selection platform 105 is further coupled, via network 115, to one or more devices of an ophthalmic practice 125. The one or more devices include a diagnostic device 130. Diagnostic device 130 is used to obtain one or more multi-dimensional images of an eye of a patient 135. Diagnostic device 130 may be any of a number of devices for obtaining multi-dimensional images of ophthalmic anatomy such as an optical coherence tomography (OCT) device, a rotating camera (e.g., a Scheimpflug camera), a magnetic resonance imaging (MM) device, and/or the like.

The ophthalmic practice 125 may also include one or more computing devices 140 for obtaining, from the diagnostic device 130, the multi-dimensional images of patient 135 and sending them to IOL selection platform 105. The one or more computing devices 140 may be one or more of a stand-alone computer, a tablet and/or other smart device, a surgical console, a computing device integrated into the diagnostic device 130, and/or the like.

IOL selection platform 105 may receive the multi-dimensional images of patient 135, extract measurements from the images, and generate a predicted $ACD_{post}$ based on the measurements and using prediction engine 120. Prediction engine may then be used to select an IOL power for patient 135. IOL selection platform 105 may then provide ophthalmic practice 125 with the predicted $ACD_{post}$ and/or selected IOL power.

Diagnostic device 130 may further be used to obtain post-operative multi-dimensional images of patient 135 after the patient undergoes cataract removal and IOL implantation using the selected IOL power provided by prediction engine 120. The one or more computing devices 140 may then send the post-operative multi-dimensional images of patient 135 to IOL selection platform 105 for use in iteratively training and/or updating the models used by prediction engine 120 so as to incorporate information from patient 135 for use with future patients.

The predicted $ACD_{post}$ and/or selected IOL power may be displayed on computing device 140 and/or another computing device, display, surgical console, and/or the like. Additionally, IOL selection platform 105 and/or the one or more computing devices 140 may identify and/or measure, in the multi-dimensional images, various characteristics of the anatomy of patient 135, as explained below in more detail. Further, IOL selection platform 105 and/or the one or more computing devices 140 may create graphical elements that identify, highlight, and/or otherwise depict the patient anatomy and/or the measured characteristics. IOL selection platform 105 and/or the one or more computing devices 140 may supplement the multi-dimensional images with the graphical elements. In some examples, the multi-dimensional images may be displayed with graphical elements overlaid on the images.

In some embodiments, IOL selection platform 105 may further include a surgical planner 150 that may be used to provide one or more surgical plans to ophthalmic practice 125 that uses the predicted $ACD_{post}$ and/or the selected IOL power.

In some embodiments, system 100 may further include a stand-alone surgical planner 160 and/or ophthalmic practice 125 may further include a surgical planner module 170 on the one or more computing device 140.

According to some embodiments, the methods described in further detail below may take advantage of measurements that may be extracted from the multi-dimensional images of ophthalmic anatomy instead of using one-dimensional on axis measurements from an optical and/or ultrasound biometer and/or white-to-white measurements taken on a front view image (e.g., a Placido image) of an eye. The one-dimensional measurements are typically suboptimal for predicting $ACD_{post}$ and selecting IOL power for a number of reasons. For example, white-to-white measurements may impart inaccuracy in IOL selection due to human error while measuring the white-to-white distance when anatomical factors such as Arcus Senilis are present. In addition, an optical and/or ultrasound biometer does not measure the angle between a pupillary axis of the pre-operative eye and a line of sight axis of the pre-operative eye when the pre-operative eye is fixated on a fixation point. Further traditional IOL selection formulas simply measure a lens thickness in one-dimension and assume that the lens has its equator at the center of the lens thickness measurement, when the typical optical lens has a longer lens thickness posterior to the lens equator than a lens thickness anterior to the lens equator.

The embodiments described in more detail herein avoid these inaccurate or suboptimal measurements through the use of multi-dimensional diagnostic images and a variety of new measurements that are superior to known measurements coming from an optical and/or ultrasound biometer for predicting $ACD_{post}$ and selecting IOL power. According to some embodiments, the measurements used to improve the prediction of $ACD_{post}$ and/or selection of IOL power may include one or more of:
  i. an angle to angle width describing the width of a line joining each of the two angular recesses of a cornea of the pre-operative eye;
  ii. an angle to angle depth measured as the perpendicular distance between an intersection point on the line joining each of the two angular recesses of the cornea of the pre-operative eye and the posterior corneal surface of the pre-operative eye;
  iii. the angle between a pupillary axis of the pre-operative eye and a line of sight axis of the pre-operative eye when the pre-operative eye is fixated on a fixation point; and/or
  iv. an estimated position of the lens equator determined as an equator line between each of two intersection points of an anterior lens radius and a posterior lens radius.

As discussed above and further emphasized here, FIG. 1 is merely an example which should not unduly limit the scope of the claims. One of ordinary skill in the art would recognize many variations, alternatives, and modifications. According to some embodiments, IOL selection platform 130 and/or one or more components of IOL selection platform, such as databases 155, prediction engine 120, and/or surgical planner 150, may be integrated into the one or more devices of ophthalmic practice 125. In some examples, computing device 140 may host IOL selection platform 105, databases 155, prediction engine 120, and/or surgical planner 150. In some examples, surgical planner 150 may be combined with surgical planner 170.

Figure 2:
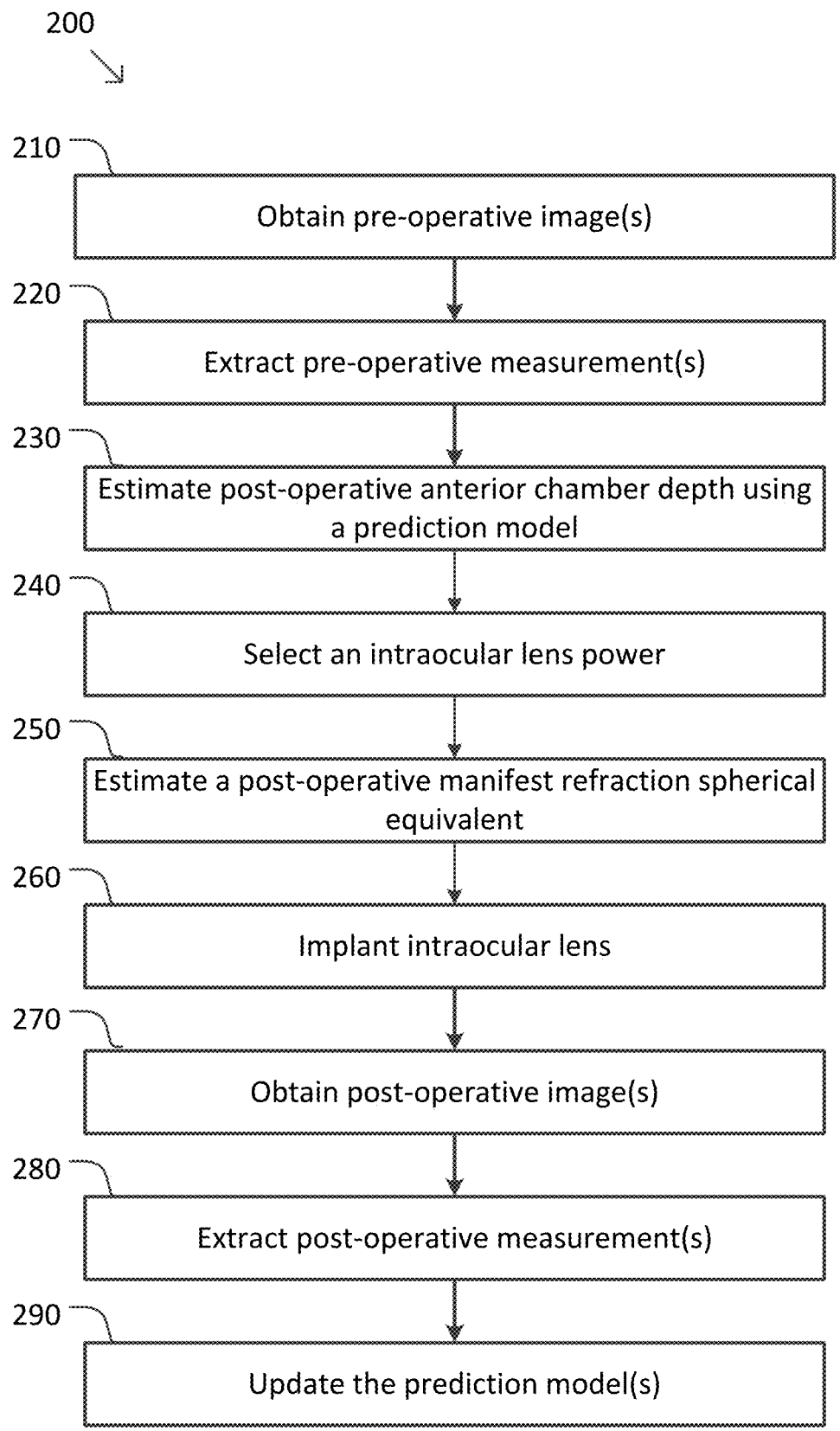
FIG. 2 is a diagram of a method of implanting an IOL using a prediction engine according to some embodiments.

FIG. 2 is a diagram of a method 200 of implanting an IOL using a prediction engine according to some embodiments. One or more of the processes 210-290 of method 200 may be implemented, at least in part, in the form of executable code stored on non-transitory, tangible, machine-readable media that when run by one or more processors (e.g., the processors of prediction engine 120, IOL prediction platform, diagnostic device 140, the one or more computing devices 140, and/or one or more of the surgical planners 150, 160, and/or 170) may cause the one or more processors to perform one or more of the processes 210-290.

At a process 210, one or more pre-operative images are obtained. In some examples, the one or more pre-operative images may include multi-dimensional images. In some examples, the one or more pre-operative images may be obtained using a diagnostic device, such as diagnostic device 130, an OCT device, a rotating (e.g., Scheimpflug) camera, an MRI device, and/or the like. In some examples, the one or more pre-operative images may be provided to a prediction engine, such as prediction engine 120.

Figure 3:
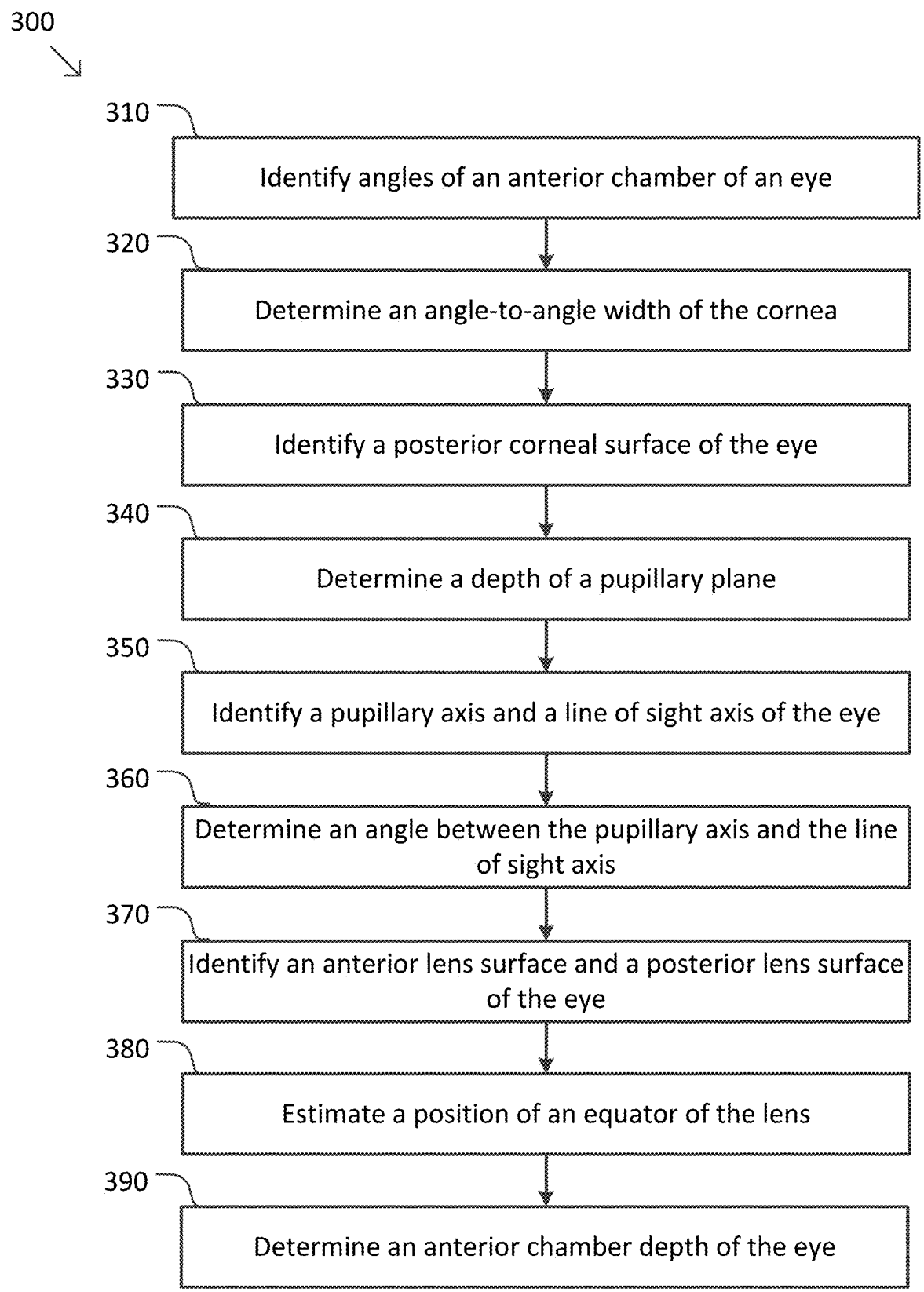
FIG. 3 is a diagram of a method of measuring characteristics of an eye according to some embodiments.

At a process 220, one or more pre-operative measurements may be extracted from the one or more pre-operative images. In some examples, the extracting may be performed by the prediction engine, such as prediction engine 120. According the some embodiments, the one or more pre-operative measurements may be extracted via measurements of various aspects of the anatomy of the eye as captured in the one or more pre-operative images according to a method 300 of measuring characteristics of an eye as shown in FIG. 3. One or more of the processes 310-390 of method 300 may be implemented, at least in part, in the form of executable code stored on non-transitory, tangible, machine-readable media that when run by one or more processors (e.g., the processors of prediction engine 120, IOL prediction platform, and/or the like) may cause the one or more processors to perform one or more of the processes 310-390. In some embodiments, process 340 is optional and may be omitted. Application of method 300 is described with respect to FIG. 4, which is a diagram of an eye 400 and characteristics of the eye according to some embodiments.

At a process 310, nasal and temporal angles 405 and 410, respectively, of an anterior chamber 480 of the eye are identified. In some examples, nasal and temporal angles 405 and 410 of anterior chamber 480 may be identified from the one or more images of the eye (e.g., the one or more pre-operative images obtained during process 210) by identifying the structures identifying the anterior chamber 480 of the eye (e.g., using one or more edge detection and/or region detection algorithms) and noting the acute angles at the edges of anterior chamber 480 located toward the temporal and nasal extents of anterior chamber 480.

At a process 320, an angle-to angle width of anterior chamber 480 is determined. In some examples, the angle-to-angle width of anterior chamber 480 corresponds to a length of line 415 between nasal and temporal angles 405 and 410 as identified during process 310.

At a process 330, a posterior corneal surface 420 of the eye is identified. In some examples, posterior corneal surface 420 may be identified from the one or more images of the eye (e.g., the one or more pre-operative images obtained during process 210) by identifying the structures which identify a cornea 475 and/or anterior chamber 480 of the eye (e.g., using one or more edge detection and/or region detection algorithms) and noting the transition between cornea 475 and anterior chamber 480.

At an optional process 340, a depth of a pupillary plane is determined. In some examples, the depth of the pupillary plane corresponds to the perpendicular distance from posterior corneal surface 420 and line 415 between the angular recesses corresponds to a length of line 425 between line 415 (as identified during process 320) and posterior corneal surface 420 (as identified during process 330), which is perpendicular to line 415 and has a longest length before reaching posterior corneal surface 420.

At a process 350, a pupillary axis 430 and a line of sight axis 435 of the eye are identified. In some examples, pupillary axis 435 corresponds to the axis formed by extending perpendicular distance line 425 determined during process 340. In some examples, line of sight axis 435 may be determined by identifying the line between a fixation point 440 to which the vision of eye 400 is fixated and fovea 445.

At a process 360, an angle κ between pupillary axis 430 and line of sight axis 435 is determined.

At a process 370, an anterior lens surface 450 and a posterior lens surface 455 of the eye are identified. In some examples, anterior lens surface 450 and/or posterior lens surface 455 may be identified from the one or more images of the eye (e.g., the one or more pre-operative images obtained during process 210) by identifying the structures identifying the lens of the eye (e.g., using one or more edge detection and/or region detection algorithms) and noting the transition between the lens and the suspensory ligaments, pupil, and/or vitreous humor of the eye.

Figure 4:
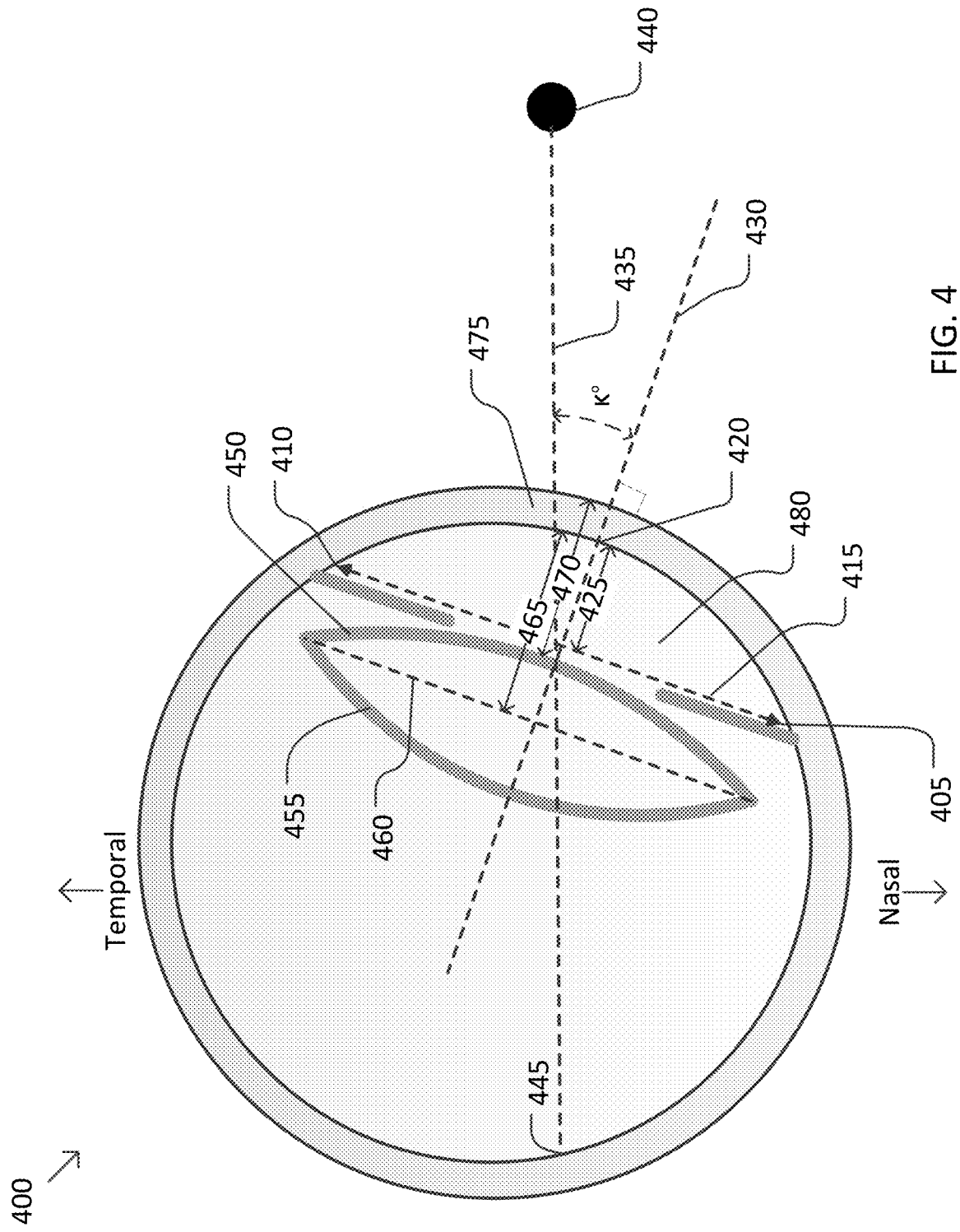
FIG. 4 is a diagram of an eye and characteristics of the eye according to some embodiments.

At a process 380, a position of an equator of the lens is determined. In the examples of FIG. 4, the equator of the lens corresponds to line 460. In some examples, the position of the lens corresponds to the perpendicular distance between the equator of the lens (e.g., line 460) and posterior corneal surface 420 as measured along pupillary axis 430. In some examples, the equator of the lens is typically not located at a midpoint between anterior lens surface 450 and posterior lens surface 455 (as identified during process 370) because the thickness of the posterior portion of the lens is typically thicker than the anterior portion of the lens. In some examples, the location of the equator of the lens (e.g., line 460) from anterior lens surface 450 may be estimated according to Equation 1, where r is half of the diameter of the lens (e.g., half the length of line 460) and R1 is a radius of anterior lens surface 450. In some examples, the location of the equator of the lens from posterior lens surface may be estimated according to Equation 2 where R2 is a radius of posterior lens surface 455. In some examples, a combination of Equations 1 and 2 may be used to determine the estimate of the location of the equator of the lens. In some examples, the radii R1 and/or R2 may be determined using a regression analysis to find a best fit circular arc to anterior lens surface 450 and posterior lens surface 455, respectively.

$$\text{Anterior Lens Thickness} = R1 - \sqrt{R1^2 - r^2} \qquad \text{Equation 1}$$

$$\text{Posterior Lens Thickness} = R2 - \sqrt{R2^2 - r^2} \qquad \text{Equation 2}$$

At a process 390, an anterior chamber depth (ACD) of the eye is determined. In the examples of FIG. 4, the ACD corresponds to the perpendicular distance 470 between posterior corneal surface 420 and anterior lens surface 450 along pupillary axis 430.

As discussed above and further emphasized here, FIG. 3 is merely an example which should not unduly limit the scope of the claims. One of ordinary skill in the art would recognize many variations, alternatives, and modifications. According to some embodiments, additional measurements of the anatomy of the eye may be determined. In some examples, the additional measurements may include a corneal power of the eye.

Referring back to FIG. 2, at a process 230 a post-operative anterior chamber depth ($ACD_{post}$) is estimated using a prediction model. In some examples, the prediction model may correspond to one of the one or more prediction models used by prediction engine 120, which has been previously trained based on previous lens implantation procedures and corresponding patient outcomes as described in further detail below with respect to process 290. In some examples, one or more of the eye characteristics determined during process 220 (e.g., one or more of an angle-to-angle width of the cornea, a depth of the pupillary plane, an angle between the pupillary axis 430 and line of sight 435 of the eye, a diameter of the lens, an estimate of a position of the lens equator, a pre-operative anterior chamber depth ($ACD_{pre}$), a corneal power, and/or the like, such as described with respect to FIGS. 3 and 4) may be provided as inputs to the prediction model, which generates the estimated $ACD_{post}$.

At a process 240, an intraocular lens (IOL) power is selected. In some examples, a recommended IOL power may be determined using a prediction model. In some examples, the prediction model may correspond to one of the one or more prediction models used by prediction engine 120, which has been previously trained based on previous lens implantation procedures and corresponding patient outcomes as described in further detail below with respect to process 290. In some examples, one or more of the eye characteristics determined during process 220 and/or the $ACD_{post}$ estimated during process 230 may be provided as inputs to the prediction model, which generates the recommended IOL power. In some examples, the prediction model used to recommend the IOL power may be a same or a different prediction model as the prediction model used to estimate $ACD_{post}$. In some examples, the recommend IOL power may be selected as the IOL power for the lens to implant or, alternatively, the surgeon or other operator may select a different IOL power based, at least in part, on the recommended IOL power.

At a process, 250, a post-operative MRSE ($MRSE_{post}$) is estimated. In some examples, the $MRSE_{post}$ may be determined using a prediction model. In some examples, the prediction model may correspond to one of the one or more prediction models used by prediction engine 120, which has been previously trained based on previous lens implantation procedures and corresponding patient outcomes as described in further detail below with respect to process 290. In some examples, one or more of the eye characteristics determined during process 220, the $ACD_{post}$ estimated during process 230, and/or the IOL power selected during process 240 may be provided as inputs to the prediction model, which generates the estimated $MRSE_{post}$. In some examples, the prediction model used to estimate the may be a same or a different prediction model as the prediction model used to estimate $ACD_{post}$ and/or the prediction model used to recommend the IOL power.

At a process 260, the IOL is implanted. In some examples, an IOL having the IOL power selected during process 240 and a size based on the position and/or diameter of the lens, and/or the like may be implanted at location corresponding to the estimated position of the equator of the lens determined during process 380.

At a process 270, one or more post-operative images may be obtained. In some examples, the one or more post-operative images may be obtained using a process similar to process 210, but after the IOL is implanted during process 260.

At a process 280, one or more post-operative measurements of the eye are obtained. In some examples, the one or more post-operative measurements may include an $ACD_{post}$ of the IOL after implantation of the IOL and/or an $MRSE_{post}$ after implantation of the IOL. In some examples, $ACD_{post}$ may be extracted using a process similar to process 390 as aided by the other processes of method 300. In some examples, the $MRSE_{post}$ may be determined based on optical measurements of the eye.

At a process 290, the one or more prediction models are updated. In some examples, the one or more pre-operative measurements extracted during process 220, the $ACD_{post}$ measurement extracted during process 280, the IOL power selected during process 240, and the $MRSE_{post}$ extracted during process may be combined to form a new training data combination. In some examples, the new training data combination may be added to the one or more of diagnostic training data sources 110. In some examples, the new training data combination may be used to iteratively improve the prediction models so that during a next use of method 200 (e.g., when method 200 is applied for a next patient) a more accurate $ACD_{post}$ may be estimated during process 230, a better recommendation for the IOL power be made during process 240, and/or a more accurate $MRSE_{post}$ may be estimated during process 250 and thus a better post-operative vision outcome for the next patient may be obtained. In some examples, the differences between the estimated $ACD_{post}$ and the actual $ACD_{post}$, the differences between the recommended IOL power and the selected IOL power, and/or the differences between the estimated $MRSE_{post}$ and the actual $MRSE_{post}$ may be used to provide training feedback (e.g., via back propagation) to the one or more models.

As discussed above and further emphasized here, FIG. 2 is merely an example which should not unduly limit the scope of the claims. One of ordinary skill in the art would recognize many variations, alternatives, and modifications. According to some embodiments, the prediction engine may be used to estimate a different measure of estimated lens position other than $ACD_{post}$. In some examples, the estimated post-operative lens position may correspond to the equator of the IOL with the estimated post-operative position of the equator of the IOL being used to select the IOL power during process 230.

In some embodiments, other predictive models (e.g., neural network models) may be trained and used to improve other aspects of method 200 including, for example, a predictive model to select the IOL power during process 240.

Figure 5A:
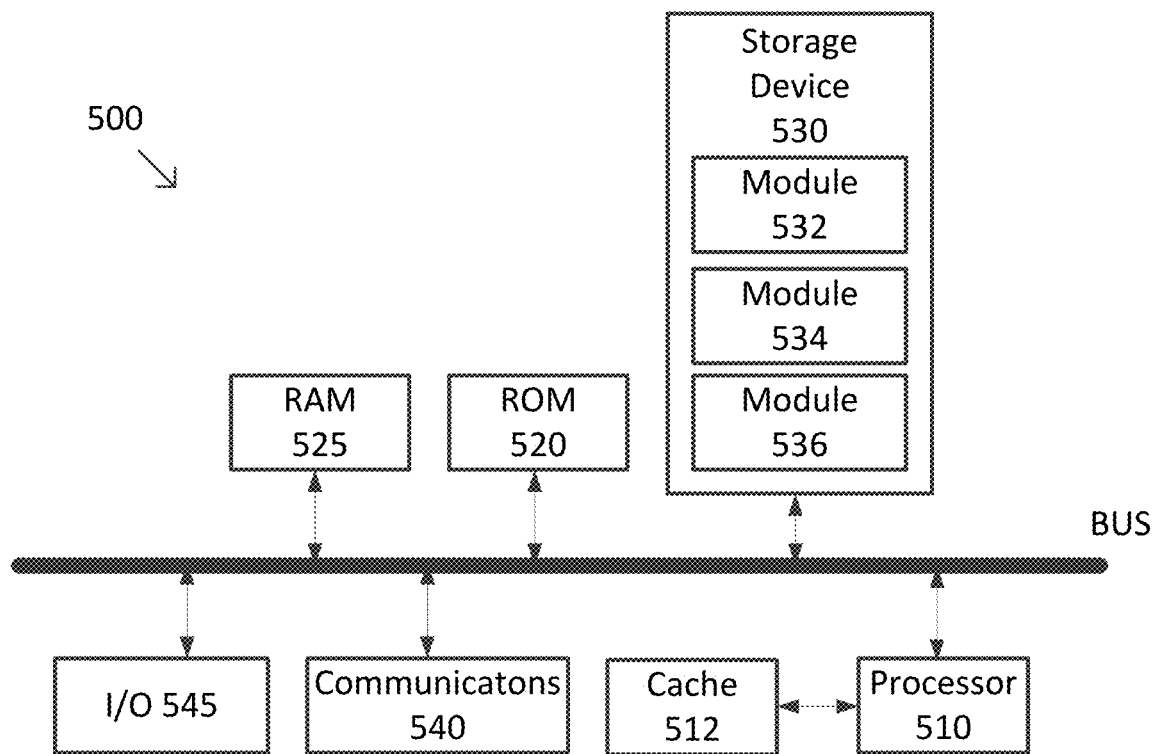
FIGS. 5A and 5B are diagrams of processing systems according to some embodiments.
Figure 5B:
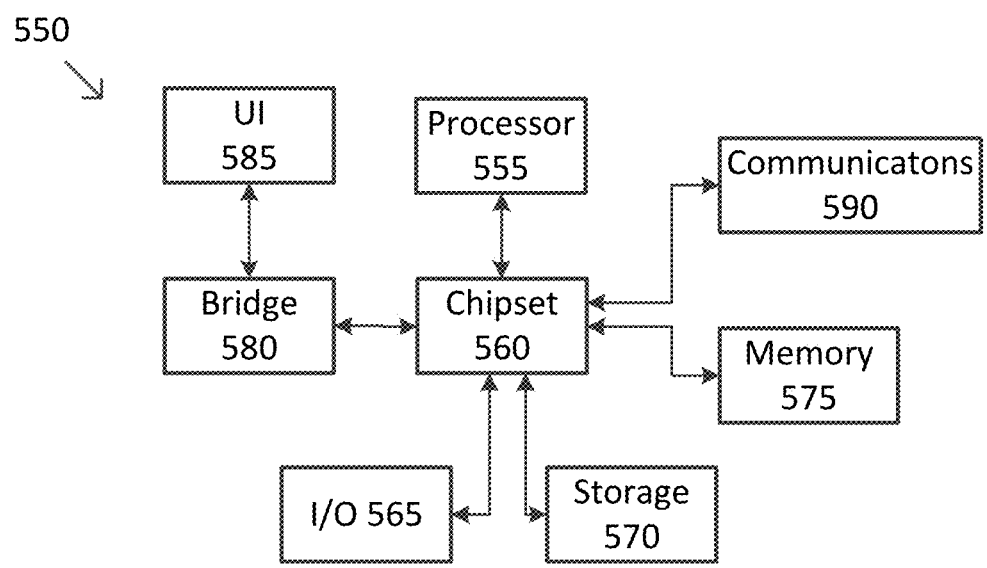

FIGS. 5A and 5B are diagrams of processing systems according to some embodiments. Although two embodiments are shown in FIGS. 5A and 5B, persons of ordinary skill in the art will also readily appreciate that other system embodiments are possible. According to some embodiments, the processing systems of FIGS. 5A and/or 5B are representative of computing systems that may be included in one or more of IOL selection platform 105, ophthalmic practice 125, prediction engine 120, diagnostic device 130, the one or more computing devices 140, any of surgical planner 150, 160, and/or 170, and/or the like.

FIG. 5A illustrates a computing system 500 where the components of system 500 are in electrical communication with each other using a bus 505. System 500 includes a processor 510 and a system bus 505 that couples various system components including memory in the form of a read only memory (ROM) 520, a random access memory (RAM) 525, and/or the like (e.g., PROM, EPROM, FLASH-EPROM, and/or any other memory chip or cartridge) to processor 510. System 500 may further include a cache 512 of high-speed memory connected directly with, in close proximity to, or integrated as part of processor 510. System 500 may access data stored in ROM 520, RAM 525, and/or one or more storage devices 530 through cache 512 for high-speed access by processor 510. In some examples, cache 512 may provide a performance boost that avoids delays by processor 510 in accessing data from memory 515, ROM 520, RAM 525, and/or the one or more storage devices 530 previously stored in cache 512. In some examples, the one or more storage devices 530 store one or more software modules (e.g., software modules 532, 534, 536, and/or the like). Software modules 532, 534, and/or 536 may control and/or be configured to control processor 510 to perform various actions, such as the processes of methods 200 and/or 300. And although system 500 is shown with only one processor 510, it is understood that processor 510 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, system 500 may be implemented as a stand-alone subsystem and/or as a board added to a computing device or as a virtual machine.

To enable user interaction with system 500, system 500 includes one or more communication interfaces 540 and/or one or more input/output (I/O) devices 545. In some examples, the one or more communication interfaces 540 may include one or more network interfaces, network interface cards, and/or the like to provide communication according to one or more network and/or communication bus standards. In some examples, the one or more communication interfaces 540 may include interfaces for communicating with system 500 via a network, such as network 115. In some examples, the one or more I/O devices 545 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 530 may include non-transitory and non-volatile storage such as that provided by a hard disk, an optical medium, a solid-state drive, and/or the like. In some examples, each of the one or more storage devices 530 may be co-located with system 500 (e.g., a local storage device) and/or remote from system 500 (e.g., a cloud storage device).

FIG. 5B illustrates a computing system 550 based on a chipset architecture that may be used in performing any of the methods (e.g., methods 200 and/or 300) described herein. System 550 may include a processor 555, representative of any number of physically and/or logically distinct resources capable of executing software, firmware, and/or other computations, such as one or more CPUs, multi-core processors, microprocessors, microcontrollers, DSPs, FPGAs, ASICs, GPUs, TPUs, and/or the like. As shown, processor 555 is aided by one or more chipsets 560, which may also include one or more CPUs, multi-core processors, microprocessors, microcontrollers, DSPs, FPGAs, ASICs, GPUs, TPUs, co-processors, coder-decoders (CODECs), and/or the like. As shown, the one or more chipsets 560 interface processor 555 with one or more of one or more I/O devices 565, one or more storage devices 570, memory 575, a bridge 580, and/or one or more communication interfaces 590. In some examples, the one or more I/O devices 565, one or more storage devices 570, memory, and/or one or more communication interfaces 590 may correspond to the similarly named counterparts in FIG. 5A and system 500.

In some examples, bridge 580 may provide an additional interface for providing system 550 with access to one or more user interface (UI) components, such as one or more keyboards, pointing/selection devices (e.g., mice, touch pads, scroll wheels, track balls, touch screens, and/or the like), audio devices (e.g., microphones and/or speakers), display devices, and/or the like.

According to some embodiments, systems 500 and/or 560 may provide a graphical user interface (GUI) suitable for aiding a user (e.g., a surgeon and/or other medical personnel) in the performance of the processes of methods 200 and/or 300. The GUI may include instructions regarding the next actions to be performed, diagrams of annotated and/or un-annotated anatomy, such as pre-operative and/or post-operative images of an eye (e.g., such as depicted in FIG. 4), requests for input, and/or the like. In some examples, the GUI may display true-color and/or false-color images of the anatomy, and/or the like.

Figure 6:
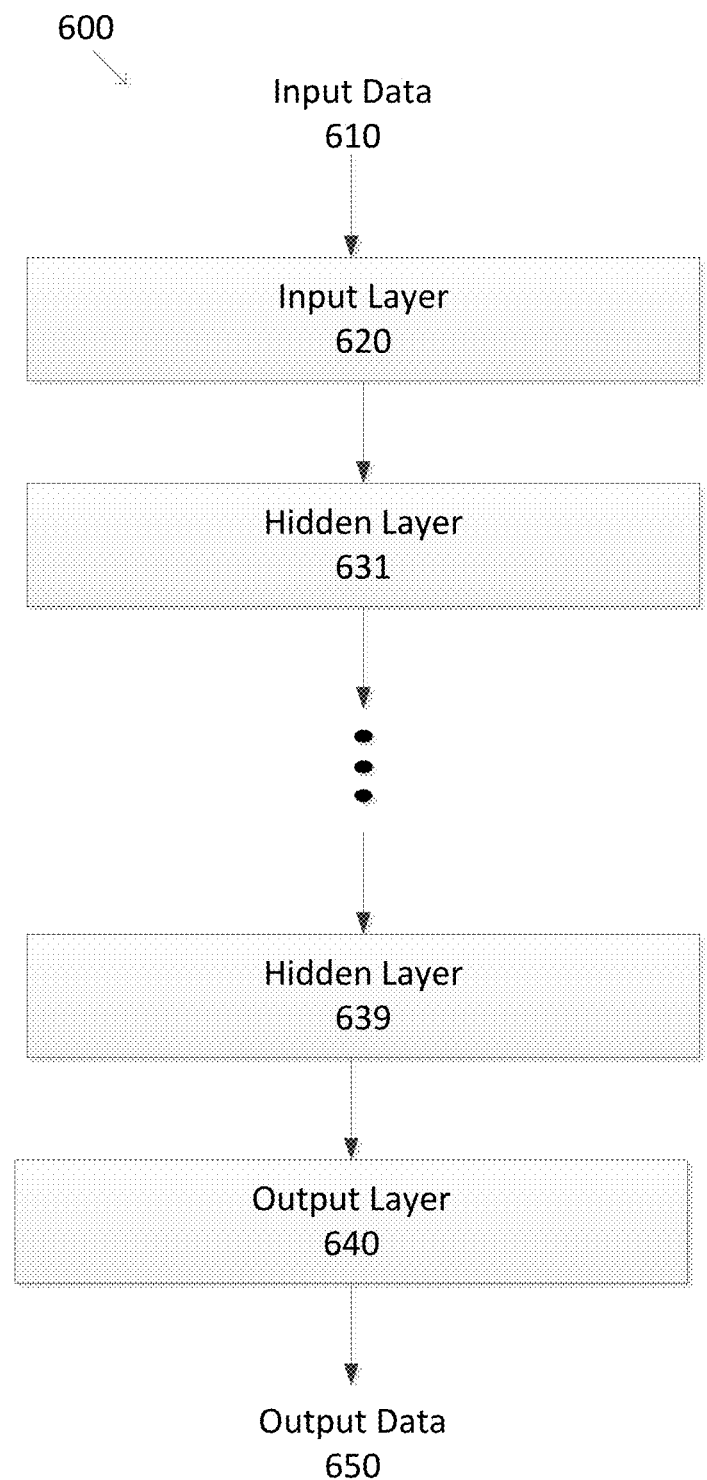
FIG. 6 is a diagram of a multi-layer neural network according to some embodiments.

FIG. 6 is a diagram of a multi-layer neural network 600 according to some embodiments. In some embodiments, neural network 600 may be representative of a neural network used to implement each of the one or more prediction models described with respect to processes 230, 240, 250, and/or 290 and used by prediction engine 120. Neural network 600 processes input data 610 using an input layer 620. In some examples, input data 610 may correspond to the input data provided to the one or more prediction models during process 230 and/or the training data provided to the one or more prediction models during the updating during process 290 used to train the one or more prediction models. Input layer 620 includes a plurality of neurons that are used to condition input data 610 by scaling, range limiting, and/or the like. Each of the neurons in input layer 620 generates an output that is fed to the inputs of a hidden layer 631. Hidden layer 631 includes a plurality of neurons that process the outputs from input layer 620. In some examples, each of the neurons in hidden layer 631 generates an output that are then propagated through one or more additional hidden layers that end with hidden layer 639. Hidden layer 639 includes a plurality of neurons that process the outputs from the previous hidden layer. The outputs of hidden layer 639 are fed to an output layer 640. Output layer 640 includes one or more neurons that are used to condition the output from hidden layer 639 by scaling, range limiting, and/or the like. It should be understood that the architecture of neural network 600 is representative only and that other architectures are possible, including a neural network with only one hidden layer, a neural network without an input layer and/or output layer, a neural network with recurrent layers, and/or the like.

In some examples, each of input layer 620, hidden layers 631-639, and/or output layer 640 includes one or more neurons. In some examples, each of input layer 620, hidden layers 631-639, and/or output layer 640 may include a same number or a different number of neurons. In some examples, each of the neurons takes a combination (e.g., a weighted sum using a trainable weighting matrix W) of its inputs x, adds an optional trainable bias b, and applies an activation function f to generate an output a as shown in Equation 3. In some examples, the activation function f may be a linear activation function, an activation function with upper and/or lower limits, a log-sigmoid function, a hyperbolic tangent function, a rectified linear unit function, and/or the like. In some examples, each of the neurons may have a same or a different activation function.

$$a=f(Wx+b) \quad \text{Equation 3}$$

In some examples, neural network 600 may be trained using supervised learning (e.g., during process 290) where combinations of training data that include a combination of input data and a ground truth (e.g., expected) output data. Differences between the output of neural network 600 as generated using the input data for input data 610 and comparing output data 650 as generated by neural network 600 to the ground truth output data. Differences between the generated output data 650 and the ground truth output data may then be fed back into neural network 600 to make corrections to the various trainable weights and biases. In some examples, the differences may be fed back using a back propagation technique using a stochastic gradient descent algorithm, and/or the like. In some examples, a large set of training data combinations may be presented to neural network 600 multiple times until an overall loss function (e.g., a mean-squared error based on the differences of each training combination) converges to an acceptable level.

Methods according to the above-described embodiments may be implemented as executable instructions that are stored on non-transitory, tangible, machine readable media. The executable instructions, when run by one or more processors (e.g., processor 510 and/or process 555) may cause the one or more processors to perform one or more of the processes of methods 200 and/or 300. Some common forms of machine readable media that may include the processes of methods 200 and/or 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method comprising: receiving, by one or more computing devices implementing a prediction engine, one or more pre-operative multi-dimensional images of an eye, wherein the pre-operative multi-dimensional images of the eye include each of: an angle to angle width describing a width of a line joining each of two angular recesses of a cornea of the eye; an angle to angle depth measured as a perpendicular distance between an intersection point on the line joining each of the two angular recesses of the cornea of the eye and a posterior corneal surface of the eye; an angle between a pupillary axis of the pre-operative eye and a line of sight axis of the eye when the eye is fixated on a fixation point; and an estimated position of a lens equator determined as an equator line between each of two intersection points of an anterior lens radius and a posterior lens radius;
   extracting, by the prediction engine, one or more pre-operative measurements of the eye based on the one or more pre-operative images of the eye; estimating, by the prediction engine using a first prediction model based on a machine learning strategy, a post-operative position of an intraocular lens based on the one or more extracted pre-operative measurements of the eye; selecting a power of the intraocular lens based on at least the estimated post-operative position of the intraocular lens;
   selecting the intraocular lens based on at least the selected power; receiving one or more post-operative multi-dimensional images of the eye after implantation of the selected intraocular lens;
   extracting one or more post-operative measurements of the eye; and updating the first prediction model based on the one or more pre-operative measurements and the one or more post-operative measurements.

2. The method of claim 1, wherein the first prediction model comprises a neural network.

3. The method of claim 1, wherein the post-operative position of the intraocular lens is an anterior corneal depth (ACD) of the intraocular lens or a position of an equator of the intraocular lens.

4. The method of claim 1, wherein selecting the intraocular lens is further based on one or more of the estimated post-operative position of the intraocular lens or a diameter of a pre-operative lens.

5. The method of claim 1, wherein the one or more pre-operative measurements include one or more of a group consisting of:
   a diameter of a pre-operative lens of the eye;
   a pre-operative anterior chamber depth of the eye, and
   a refractive power of a cornea of the eye.

6. The method of claim 1, wherein selecting the power comprises recommending, by the prediction engine using a second prediction model, a recommended power for the intraocular lens based on at least the estimated post-operative position.

7. The method of claim 6, further comprising updating the second prediction model based on the recommended power and the selected power.

8. The method of claim 1, further comprising estimating, by the prediction engine using a second prediction model, a post-operative manifest refraction spherical equivalent (MRSE) based on at least the estimated post-operative position and the selected power.

9. The method of claim 8, further comprising:
   measuring an actual power-operative MRSE; and
   updating the second prediction model based on the estimated post-operative MRSE and the actual power-operative MRSE.

10. The method of claim 1, wherein the one or more pre-operative multi-dimensional images are each received from a diagnostic device selected from a group consisting of an optical coherence tomography (OCT) device, a rotating Scheimpflug camera, and a magnetic resonance imaging (MRI) device.

11. The method of claim 1, further comprising planning one or more procedures for implantation of the intraocular lens.

12. The method of claim 1, further comprising displaying one of the one or more pre-operative multi-dimensional images annotated with one of the one or more extracted pre-operative measurements.

13. A prediction engine comprising: one or more processors; wherein the prediction engine is configured to: receive one or more pre-operative multi-dimensional images of an eye obtained by a diagnostic device, wherein the pre-operative multi-dimensional images of the eye include each of: an angle to angle width describing a width of a line joining each of two angular recesses of a cornea of the eye; an angle to angle depth measured as a perpendicular distance between an intersection point on the line joining each of the two angular recesses of the cornea of the eye and a posterior corneal surface of the eye; an angle between a pupillary axis of the pre-operative eye and a line of sight axis of the eye when the eye is fixated on a fixation point; and an estimated position of a lens equator determined as an equator line between each of two intersection points of an anterior lens radius and a posterior lens radius; extract one or more pre-operative measurements of the eye based on the one or more pre-operative images of the eye; estimate, using a first prediction model based on a machine learning strategy, a post-operative position of an intraocular lens based on the one or more extracted pre-operative measurements of the eye; recommend a power of the intraocular lens based on at least the estimated post-operative position of the intraocular lens; provide the recommended power to a user to facilitate selection of the intraocular lens for implantation; receive one or more post-operative multi-dimensional images of the eye after implantation of the selected intraocular lens; extract one or more post-operative measurements of the eye; and update the first prediction model based on the one or more pre-operative measurements and the one or more post-operative measurements.

14. The prediction engine of claim 13, wherein the post-operative position of the intraocular lens is an anterior corneal depth (ACD) of the intraocular lens or a position of an equator of the intraocular lens.

15. The prediction engine of claim 13, wherein the one or more pre-operative measurements include one or more of a group consisting of:

a diameter of a pre-operative lens of the eye;
a pre-operative anterior chamber depth of the eye, and
a refractive power of a cornea of the eye.

16. The prediction engine of claim 13, further comprising estimating, by the prediction engine using a second prediction model, a post-operative manifest refraction spherical equivalent (MRSE) based on at least the estimated post-operative position and a selected power of the intraocular lens.

17. A non-transitory machine-readable medium comprising a plurality of machine-readable instructions which when executed by one or more processors are adapted to cause the one or more processors to perform a method comprising: receiving one or more pre-operative multi-dimensional images of an eye, wherein the pre-operative multi-dimensional images of the eye include each of: an angle to angle width describing a width of a line joining each of two angular recesses of a cornea of the eye; an angle to angle depth measured as a perpendicular distance between an intersection point on the line joining each of the two angular recesses of the cornea of the eye and a posterior corneal surface of the eye; an angle between a pupillary axis of the pre-operative eye and a line of sight axis of the eye when the eye is fixated on a fixation point; and an estimated position of a lens equator determined as an equator line between each of two intersection points of an anterior lens radius and a posterior lens radius; extracting one or more pre-operative measurements of the eye based on the one or more pre-operative images of the eye; estimating, using a prediction model based on a machine learning strategy, a post-operative position of an intraocular lens based on the one or more extracted pre-operative measurements of the eye; recommending a power of the intraocular lens based on at least the estimated post-operative position of the intraocular lens; providing the recommended power to a user to facilitate selection of the intraocular lens for implantation; receiving one or more post-operative multi-dimensional images of the eye after implantation of the selected intraocular lens; extracting one or more post-operative measurements of the eye; and updating the prediction model based on the one or more pre-operative measurements and the one or more post-operative measurements.

* * * * *